(12) United States Patent
Kurita et al.

(10) Patent No.: US 7,504,114 B1
(45) Date of Patent: Mar. 17, 2009

(54) PREPARATIONS FOR PERCUTANEOUS ABSORPTION

(75) Inventors: Hisakazu Kurita, Tsukuba (JP); Tetsuro Tateishi, Tsukuba (JP); Tatsuaki Suzuki, Tsukuba (JP); Naruhito Higo, Tsukuba (JP)

(73) Assignee: Hisamitsu Pharmaceuticals, Saga (JP)

( * ) Notice: Subject to any disclaimer, the term of this patent is extended or adjusted under 35 U.S.C. 154(b) by 0 days.

(21) Appl. No.: 09/958,624

(22) PCT Filed: Apr. 7, 2000

(86) PCT No.: PCT/JP00/02266

§ 371 (c)(1), (2), (4) Date: Oct. 12, 2001

(87) PCT Pub. No.: WO00/61120

PCT Pub. Date: Oct. 19, 2000

(30) Foreign Application Priority Data

Apr. 13, 1999 (JP) ................. 11/104828

(51) Int. Cl.
*A61K 9/70* (2006.01)
*A61L 15/16* (2006.01)

(52) U.S. Cl. ............... 424/449; 424/443; 424/444; 424/447

(58) Field of Classification Search ............ 424/401, 424/443–449, 450
See application file for complete search history.

(56) References Cited

U.S. PATENT DOCUMENTS

| 3,472,931 | A | | 10/1969 | Stoughton | |
|---|---|---|---|---|---|
| 4,017,641 | A | | 4/1977 | DiGiulio | |
| 4,695,465 | A | * | 9/1987 | Kigasawa et al. | 424/449 |
| 4,859,696 | A | * | 8/1989 | Kayima et al. | 514/420 |
| 5,211,943 | A | * | 5/1993 | Azuma et al. | 424/448 |
| 5,411,740 | A | * | 5/1995 | Lee et al. | 424/448 |
| 5,866,157 | A | * | 2/1999 | Higo et al. | 424/448 |
| 5,879,690 | A | * | 3/1999 | Perricone | 424/401 |
| 6,139,866 | A | * | 10/2000 | Chono et al. | 424/443 |
| 6,203,817 | B1 | * | 3/2001 | Cormier et al. | 424/464 |

FOREIGN PATENT DOCUMENTS

| EP | 0 580 074 A1 | | 1/1994 |
|---|---|---|---|
| JP | 56-061312 | | 5/1981 |
| JP | 61-249934 | | 11/1986 |
| JP | 62-126119 | | 6/1987 |
| JP | 62-181226 | | 8/1987 |
| JP | 63-079820 | | 4/1988 |
| JP | 63-159315 | | 7/1988 |
| JP | 5-946 | | 1/1993 |
| JP | 05-025039 | | 2/1993 |
| JP | 6-40947 | | 2/1994 |
| JP | 9-208464 | | 8/1997 |
| JP | 10-204001 | | 8/1998 |
| WO | WO96/16642 | * | 6/1996 |
| WO | WO 96/16642 | | 6/1996 |
| WO | WO97/42952 | * | 11/1997 |
| WO | WO 97/42952 | | 11/1997 |

OTHER PUBLICATIONS

S. Gorukanti et al., *International Journal of Pharmaceutics*, 192:159-172 (1999).

* cited by examiner

*Primary Examiner*—Michael G Hartley
*Assistant Examiner*—Micah-Paul Young
(74) *Attorney, Agent, or Firm*—Edwards Angell Palmer & Dodge LLP; Peter F. Corless; Dwight D. Kim (57) ABSTRACT

Preparations for percutaneous absorption comprising a basic drug or its salt dissolved in a liquid component and having an enhanced percutaneous absorbability and a safety to the skin, i.e., the administration site. The preparations for percutaneous absorption, preferably patches, contain a basic drug or its salt, an organic acid or its salt and a liquid component having a solubility parameter of from 7 to 13 $(\text{cal/cm}^3)^{1/2}$ and a have a very excellent skin permeability of the drug.

3 Claims, 8 Drawing Sheets

PREPARATIONS FOR PERCUTANEOUS ABSORPTION

TECHNICAL FIELD

The present invention relates to preparations for percutaneous absorption containing a basic drug or salt, an organic acid or its salt and a liquid component having a solubility parameter ranging from 7 to 13 $(cal/cm^3)^{1/2}$ and have a very excellent skin permeability of the drug.

BACKGROUND ART

With regard to methods for administration of drugs, oral administration, rectal administration, percutaneous administration and intravenous administration have known. Among them, oral administration is widely used. In case of oral administration, however, administered drug has disadvantages to receive the first-pass effect after absorption and to show a temporally excessive over blood concentration after administration. Further, in oral administration, many adverse effects such as gastrointestinal trouble, vomiting sensation and anorexia have reported. In addition, in the recent aging society, numbers of patients with dysphagia are increased, and easily ingestible preparations are required from the clinical standpoint.

As a result, development of preparations for percutaneous administration has positively promoted for the purpose of solving such disadvantages of oral administration and obtaining easily ingestible preparations for patients with safety and repeatedly, and such the improved preparations are launched in the market.

However, percutaneous absorbability of drug in such preparations for percutaneous absorption is still insufficient. In addition, since many drugs have low percutaneous absorbability, development of the preparations for percutaneous absorption is difficult and the objectives for absorption have not successful. Namely, since the normal skin has barrier function for protecting infiltration of foreign matters into the body, base ingredients used in the conventional preparations for percutaneous absorption can not reveal sufficient percutaneous absorption of the combined active ingredient.

For that solution, a contrivance for increasing percutaneous absorption of drug through the stratum corneum of skin is required, and in general so called a promoter for percutaneous absorption is combined with the base ingredient. For example, a combination of absorption promoter of lower alkylamide such as dimethyl acetamide and ethyl alcohol, isopropyl alcohol or isopropyl palmitate (U.S. Pat. No. 3,472,931); a combination of 2-pyrrolidone and proper oil or that of straight chain fatty acid and alcohol ester (U.S. Pat. No. 4,017,641); and a combination of lower alcohol and $C_{7-20}$ alcohol, $C_{5-30}$ aliphatic cyclic hydrocarbon, $C_{19-26}$ aliphatic carboxylic acid alcohol ester, $C_{10-24}$ mono- or di-ether or $C_{11-15}$ ketone and water (JP-A-61-249934) have proposed. However, these conventional absorption promoters and the composition of absorption promoter are not sufficiently safe on the skin. Further, in case of the preparations for percutaneous absorption containing salt of basic drug, its effect can not be expected.

Examples of preparations for percutaneous administration such as a combination of drug and organic acid have reported. For example, tapes combining betamethasone valerate and organic acid in natural rubber adhesives (JP-B-63-45368), tapes combining steroid antiinflammatory agent and organic acid in acrylic adhesives (JP-B-7-47535), and cataplasms combining methyl salicylate as an active ingredient, emulsifier, organic acid, plasticizer, adhesive resin and water in polymer of styrene-isoprene-styrene block copolymer (JP-B-3-31685) have proposed. Objectives of these organic acids are, however, improvement of stability, improvement of solubility and pH adjuster. Further, since these drugs are acidic or neutral, objectives of these preparations are not to improve skin permeability of bioactive substance through formation of ion pair, which is an object to use organic acids in the present invention.

Means for improving skin permeability of basic bioactive substances are known. For example, tapes combining citric acid and isoproterenol hydrochloride in acrylic adhesives (JP-A-63-79820), and tapes combining organic acid and vinpocetine in acrylic adhesives (JP-A-5-25039) have reported. These preparations have problems such as irritation in detaching and no sufficient effect for treatment in release of drugs.

Means for combining drug and organic acid have reported as preparations for percutaneous administration. For example, a preparation containing organic acid and glycol in nonsteroidal antiinflammatory agent (JP-A-62-181226), and a patch containing alkaline metal salt of nonsteroidal antiinflammatory agent and free nonsteroidal antiinflammatory agent as well as stronger organic acid (JP-B-7-47535) have reported. These inventions relate to acidic drugs and not to basic drugs. Examples of combination of basic drug or its salt, $C_{2-5}$ alcohol, $C_{2-5}$ organic acid and $C_{16-20}$ carboxylic acid ester have known, but no use of organic acid salt is described. In WO 96/16642, patch preparation with a salt of basic drug containing organic acid salt is disclosed, but the fact that organic acid salt increases solubility of basic drug salt in the liquid component having specific solubility parameter ranging from 7 to 13 $(cal/cm^3)^{1/2}$ is not disclosed. In the prior known inventions, preparations for percutaneous absorption, in which basic drug in the form of salt is dissolved in a liquid component to achieve percutaneous absorption of drug, have not known.

DISCLOSURE OF INVENTION

The present invention is contemplated to solve problems of the above-described prior arts. It is an aspect of the present invention to provide preparations for percutaneous absorption with improved percutaneous absorption of drugs by dissolving basic drug or its salt in a liquid component, as well as safety for the skin of the administration site.

Example of the preparations for percutaneous absorption of the present invention is preferably a patch, and more preferably the nonaqueous patch without substantially containing water.

Compositions and forms of the preparations for percutaneous absorption of the present invention are explained as follows.

Salt of drug used in the preparations for percutaneous absorption of the present invention is not limited, if it is a basic drug salt, in which the solubility to the liquid component having the solubility parameter ranging from 7 to 13 $(cal/cm^3)^{1/2}$ is increased in the presence of organic acid salt or inorganic acid salt. Examples drugs are hypnotics and sedatives (flurazepam hydrochloride and rilmazafone), antipyretic antiinflammatory agents (butorphanol tartrate and perixazole citrate), analeptics and antihypnotics (methamphetamine hydrochloride and methylphenidate hydrochloride), psychoneural drugs (chlorpromazine hydrochloride, imipramine hydrochloride, fluvoxamine maleate and sertraline hydrochloride), local anesthetics (lidocaine hydrochloride and procaine hydrochloride), urinary system drugs (oxybutynin hydrochloride), skeletal muscle relaxant (tizanidine hydrochloride, eperisone hydrochloride and pridinol mesylate), autonomic drugs (calpronium chloride and neostigmine bromide), drugs for Parkinson's disease (pergolide mesylate, bromocriptine mesylate, trihexyphenidyl hydrochloride and amantadine hydrochloride), antihistamines (clemastine fumarate and diphenhydramine tannate), bronchodilators (tulobuterol hydrochloride and procaterol hydrochloride), cardiotonics (isoprenaline hydrochloride and dopamine hydrochloride), coronary vasodilator (diltiazem hydrochloride and verapamil hydrochloride), peripheral vasodilator (nicatamate citrate and trazoline hydrochloride), drugs for circulatory system (flunarizine hydrochloride, nicardipine hydrochloride, benidipine hydrochloride and efonidipine hydrochloride), antiarrhythmic drugs (propranolol hydrochloride and alprenolol hydrochloride), antiallergic agent (ketotifen fumarate and azelastine hydrochloride), antivertigenous drug (betahistine mesylate and diphenydol hydrochloride), serotonin receptor antagonist antiemetics and narcotic analgesics (morphine sulfate and fentanyl citrate), and pharmacologically acceptable acid addition salt thereof.

Further, examples of free forms of drugs are not limited and are basic drugs, in which the solubility to the liquid component having the solubility parameter ranging from 7 to 13 $(cal/cm^3)^{1/2}$ is increased by organic acid or inorganic acid. These include free forms of the above drugs.

In addition, these drugs can be used alone or in combination with two or more drugs, or in any forms of drug with inorganic salt or organic salt thereof can be included. Amount of combination of these drugs depends on types of open squares show a comparative example without acetic acid (comparative example 8-B).

BEST MODE FOR CARRYING OUT THE INVENTION

We have continued extensive studies in order to solve these problems and found that in the patch preparations containing basic drug in the form of salt, when specific amount of organic acid salt is contained, solubility of drug in the liquid component, a base component, is improved through the formation of ion pairs, and the skin permeability of drug is significantly improved as a result of increasing a partition ratio into the skin, as well as showing safety to the administration site of skin, and completed to solve the prior problems. We have also found that, in case of basic drug (free form), when specific amount of organic acid (free form) is contained in the patch containing the basic drug, skin permeation of drug is improved though the formation of ion pairs. Specifically advantageous effective organic acid salt is sodium acetate, and organic acid is acetic acid. As a result of our extensive studies, we have found that in case of a liquid component having a solubility parameter ranging from 7 to 13 $(cal/cm^3)^{1/2}$, solubility of drug is increased and skin permeability of the drug is improved.

It is an aspect of the present invention to provide preparations for percutaneous absorption comprising a basic drug or its salt, an organic acid or its salt and a liquid component having a solubility parameter ranging from 7 to 13 $(cal/cm^3)^{1/2}$. More particularly, the aspect of the present invention is to provide the preparations for percutaneous drugs and is approximately 0.1-50 wt % to total weight of the preparations for percutaneous absorption. In case of patch preparation for percutaneous absorption of the present invention, drugs are preferably formulated in an amount ranging from 0.1 to 20 wt %, depending on total weight of composition of the adhesive layer, by considering sufficient permeable amount of drug and irritability to the skin such as flare as the patch preparation.

Examples of organic acid or its salt used in the preparations for the percutaneous absorption are aliphatic (mono, di or tri)

carboxylic acid (for example, acetic acid, propionic acid, isobutyric acid, caproic acid, caprylic acid, lactic acid, maleic acid, pyruvic acid, oxalic acid, succinic acid, citric acid and malic acid), aromatic carboxylic acid (for example, phthalic acid, salicylic acid, benzoic acid and acetylsalicylic acid), alkylsulfonic acid (for example, ethanesulfonic acid, propylsulfonic acid, butanesulfonic acid and polyoxyethylene alkyl ether sulfonic acid), alkylsulfonic acid derivatives (for examples, N-2-hydroxyethylpiperidine-N'-2-ethane sulfonic acid (hereinafter designates as "HEPES") and cholic acid derivatives (for example, dehydrocholic acid) or water soluble inorganic salt thereof. Among them, $C_{2-10}$ carboxylic acid or metal salt thereof is preferable, and more preferably sodium acetate or acetic acid. These organic acids or salt thereof can be anhydride or hydrate, and in case that the preparation for percutaneous absorption is the patch and the organic acid or salt thereof is used in the hydrophobic adhesive layer, the anhydride is preferable.

These organic acid or salt thereof can be prescribed, by considering sufficient permeability and irritation to the skin as the preparation for percutaneous absorption, preferably at 0.01-20 wt %, more preferably at 0.1-15 wt %, most preferably at 0.1-10 wt %, based on total weight of the composition of the preparation for percutaneous absorption (adhesive layer in case that the preparation for percutaneous absorption is patch). Ratio of combination of the basic drug salt and the organic acid salt or that of basic drug and the organic acid are preferably 5/1-1/5 (molar ratio).

The liquid component of the present invention is not specifically limited, if it has the solubility parameter δ, which is an index of lipophilicity, ranging from 7 to 13 $(cal/cm^3)^{1/2}$ and is liquid state at room temperature. The solubility parameter can be found by referring with the solubility parameter of various substance described in "Polymer Handbook" published by A Wiley-International Publication, or can be calculated by R. F. Fedors, "Polymer Engineering and Science", 14(2), 147-154, 1974. Among them, liquid paraffin (solubility parameter δ=8.1), isopropyl myristate (δ=8.5), crotamiton (δ=9.9), triacetin (δ=10.2), oleic acid (δ=7.7), oleyl alcohol (δ=8.1), triethyl citrate (δ=11.5), silicone oil (δ=7.4), propylene glycol (δ=12.6), 1-[2-(decylthio) ethyl]azacyclopentane-2-one (hereinafter, general term "pirotiodecane" will be used)(δ=9.6) and diethyl sebacate (δ=9.3) are preferable and two or more of these compound can also be used. In case of dissolving the basic drug or its salt in the liquid component, the process of powdering, agitating and heating with the organic acid or its salt is effective.

The liquid component can be formulated in an amount of 3.0-70 wt % in total.

Absorption promoters which can be used are any compounds which have absorption promoter action in the skin. Examples thereof are C6-20 fatty acids, aliphatic alcohols, fatty acid esters or ethers, aromatic organic acids, aromatic alcohols, aromatic organic acid esters or ethers (these may be saturated or unsaturated, or cyclic, straight or branched chains), further lactates, acetates, monoterpenes, sesquiterpenes, Azone, Azone derivatives, glycerate fatty acid esters, sorbitan fatty acid esters (Span), polysorbates (Tween), polyethylene glycol fatty acid esters, polyoxyethylene hydrogenated castor oil (HCO) and sucrose esters of fatty acid.

Preferable concrete examples are caprylic acid, capric acid, caproic acid, lauric acid, myristic acid, palmitic acid, stearic acid, oleic acid, linoleic acid, linolenic acid, lauryl alcohol, myristyl alcohol, oleyl alcohol, cetyl alcohol, methyl laurate, isopropyl mylistate, myristyl mylistate, octyldodecyl mylistate, cetyl palmitate, salicylic acid methyl salicylate, salicylic acid ethylene glycol, cinnamic acid, methyl cinnamate, cresol, cetyl lactate, ethyl acetate, propyl acetate, geraniol, thymol, eugenol, terpineol, 1-menthol, borneol, d-limonene, isoeugenol, isoborneol, nerol, dl-camphor, glycerol monolaurate, glycerol monooleate, sorbitan monolaurate, sucrose monolaurate, polysorbate 20, propylene glycol, polyethylene glycol monolaurate, polyethylene glycol monostearate, HCO-60 and pirotiodecane. Among them, lauryl alcohol, 1-menthol, propylene glycol and pirotiodecane are preferable.

These absorption promoters can be prescribed, by considering sufficient permeability and irritation to the skin, such as flare and edema, as the preparation for percutaneous absorption, preferably at 0.01-20 wt %, more preferably at 0.1-15 wt %, most preferably at 0.1-10 wt %, based on total weight of the composition of the preparation for percutaneous absorption (adhesive layer in case that the preparation for percutaneous absorption is patch).

The preparations for percutaneous absorption of the present invention are preferably patches, especially in case of patches, nonaqueous system preparations for percutaneous preparation without containing water.

Examples of plasticizers of the adhesive layer of the patch preparations are preferably petroleum oil (such as paraffin processed oil, naphthene processed oil and aromatic processed oil), squalane, squalene, vegetable oil (such as olive oil, camellia oil, caster oil, tall oil and peanut oil), silicone oil, dibasic acid ester (such as dibutylphthalate and dioctylphthalate), liquid rubber (such as polybutene and liquid isoprene rubber), diethyleneglycol, polyethylene glycol, glycol salicylate, propylene glycol, dipropylene glycol, triacetin, triethyl citrate, crotamiton and diethyl sebacate. Among them, especially, liquid paraffin, liquid polybutene, glycol salicylate, crotamiton and diethyl sebacate are preferable.

These components can be used with mixing two or more compounds. Amounts of mixing these plasticizers based on total composition of the adhesive layer can be, by considering with sufficient permeability and sufficient coagulation power as the patches, 5-70 wt %, preferably 5-60 wt %, more preferably 5-50 wt %.

Examples of lipophilic hydrophobic polymer used in the adhesive layer of the patches are styrene-isoprene-styrene block copolymer (hereinafter designates as SIS), isoprene rubber, polyisobutylene (hereinafter designates as PIB), styrene-butadiene-styrene block copolymer (hereinafter designates as SBS), styrene-butadiene rubber (hereinafter designates as SBR) and acrylic polymer (copolymer with at least two of 2-ethylhexyl acrylate, vinyl acetate, methacrylate, methoxyethyl acrylate and acrylic acid). Especially, SIS, PIB or blending of these two polymers and acrylic polymers are preferable.

Amount of mixing these hydrophobic polymers in the adhesive layer based on total weight of the composition can be, by considering with formation of the adhesive layers and sufficient permeability, 5-60 wt %, preferably 10-50 wt %, more preferably 15-40 wt % in SIS and PIB. Further, in acrylic polymer, these can be 10-98 wt %, preferably 20-98 wt %, more preferably 30-98 wt %.

Examples of adhesive additive resins used in the adhesive layer in patches are rosin derivatives (for example, rosin, rosin glycerol ester, hydrogenated rosin, hydrogenated rosin glycerol ester and rosin pentaerythritol ester), alicyclic saturated hydrocarbon resin, aliphatic hydrocarbon resin, terpene resin and maleate resin.

Especially, hydrogenated rosin glycerol ester, alicyclic saturated hydrocarbon resin, aliphatic hydrocarbon resin and terpene resin are preferable.

Amount of mixing the adhesive additive resin based on total composition of the adhesive layer can be, by considering with sufficient adhesive power as the patches and irritation to skin at removal, 10-70 wt %, preferably 15-60 wt %, more preferably 20-50 wt %.

In addition, if necessary, antioxidants, fillers, crosslinking agents, antiseptics and UV absorbers can be used. Examples of antioxidants are tocopherol and ester derivatives thereof, ascorbic acid, stearyl ascorbate, nordihydroguaiaretic acid, dibutyldihydrotoluene (BHT) and butyl hydroxy anisole. Examples of fillers are calcium carbonate, magnesium carbonate, silicate (for example, aluminum silicate and magnesium silicate), silicic acid, barium sulfate, calcium sulfate, calcium zincate, zinc oxide and titanium oxide. Examples of crosslinking agents are amino resin, phenolic resin, epoxy resin, alkyd resin, thermosetting resin such as unsaturated polyester, isocyanates, block isocyanates, organic crosslinking agents, and inorganic crosslinking agents such as metal or metallic compound. Examples of antiseptics are ethyl p-hydroxybenzoate, propyl p-hydroxybenzoate and butyl p-hydroxybenzoate. Examples of UV absorber are p-aminobenzoic acid derivatives, anthranilic acid derivatives, salicylic acid derivatives, coumalin derivatives, amino acids, imidazoline derivatives, pyrimidine derivatives and dioxane derivatives.

These antioxidants, fillers, crosslinking agents, antiseptics and UV absorbers, in total, can be mixed, based on total weight of compositions of the adhesive layers in patches, preferably 10 wt % or less, more preferably 5 wt % or less, most preferably 2 wt % or less.

The adhesive layers having these compositions can be produced by any methods. For example, base composition containing drug is melted by heating, spread on a release paper or a supporting material, and joined together with the supporting material or the release paper to obtain the patch of the present invention. Alternatively, base composition containing drug is dissolved in solvent such as toluene, hexane or ethyl acetate, spread on a release paper or a supporting material, and after removal of solvent and dried, joined together with the supporting material or the release paper to obtain the patch of the present invention.

As long as the adhesive layer of the patches in the preparation for percutaneous absorption of the present invention is constituted by the above composition containing the organic acid or its salt and the drug, the other constitutions and materials of each constitutional part of the patches can be freely constructed in any types.

The patches can be comprised of the above adhesive layers, the supporting layer to support the adhesive layer and the release paper layer provided on the adhesive layer.

Elastic or non-elastic supporting materials can be used for the supporting material. For example, cloth, nonwoven fabric, polyurethane, polyester, poly(vinyl acetate), poly(vinylidene chloride), polyethylene, poly(ethylene terephthalate) and aluminum sheet or composite materials thereof can be selected and used.

As long as the preparations for percutaneous absorption of the present invention are constituted by the above composition containing the basic drug or its salt, the organic acid or its salt and the liquid component having the solubility parameter ranging from 7 to 13 $(cal/cm^3)^{1/2}$, the other constitution and materials of respective constitutional parts can be freely constructed in any types. However, in order to dissolve basic drug or its salt into the base composition, better result can be obtained by powdering, agitating or heating the basic drug and organic acid or its salt in together.

The preparations for percutaneous absorption of the present invention can provide superior skin permeability, less skin irritation, superior content uniformity of drug or physical stability of base.

The present invention is more concretely explained by illustrating examples of the present invention, but the present invention is not limited within these examples, and various modifications may be possible within the technical scope of the present invention.

EXAMPLES

In the examples, "%" means percent by weight.

Measurement of solubility

Solubility of salt of basic drug to the liquid component (liquid paraffin, isopropyl myristate, crotamiton, triacetin, oleic acid, oleyl alcohol, triethyl citrate, silicone oil, propylene glycol, pirotiodecane, ethylene glycol and water) was measured.

Example 1

Figure 1:
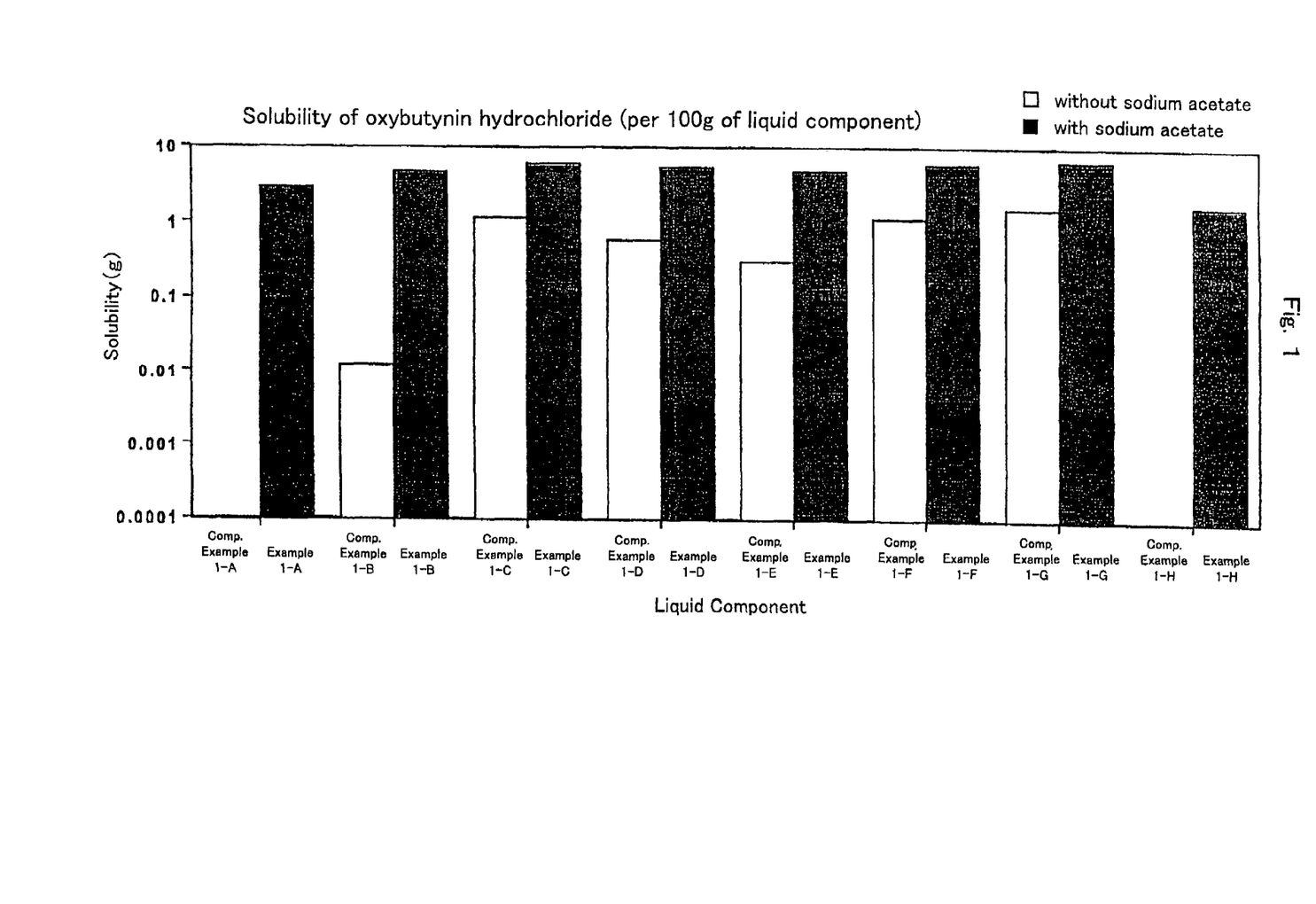
FIG. 1 shows solubility of oxybutynin hydrochloride as a basic drug salt in various liquid components. In the figure, open bar graphs indicate without addition of organic acids and closed bar graphs indicate with addition of organic acid salt of the present invention.

Liquid components, liquid paraffin (example 1-A), isopropylmyristate (example 1-B), crotamiton (example 1-C), triacetin (example 1-D), oleic acid (example 1-E), oleyl alcohol (example 1-F), triethyl citrate (example 1-G) and silicone oil (example 1-H), respectively, 10 g, sodium acetate 0.1 g and excess amount of oxybutynin hydrochloride were mixed well in the mortar for 30 minutes. Subsequently, the mixture was transferred into vials and stirred at room temperature for 12 hours. The mixture was filtered using the filter and concentration of oxybutynin hydrochloride in the filtrate was measured. Results are shown in FIG. 1.

Comparative Example 1

Liquid components, liquid paraffin (comparative example 1-A), isopropylmyristate (comparative example 1-B), crotamiton (comparative example 1-C), triacetin (comparative example 1-D), oleic acid (comparative example 1-E), oleyl alcohol (comparative example 1-F), triethyl citrate (comparative example 1-G) and silicone oil (comparative example 1-H), respectively, 10 g, and excess amount of oxybutynin hydrochloride were mixed well in the mortar for 30 minutes. Subsequently, the mixture was transferred into vials and stirred at room temperature for 12 hours. The mixture was filtered using the filter and concentration of oxybutynin hydrochloride in the filtrate was measured. Results are shown in FIG. 1.

Example 2

Figure 2:
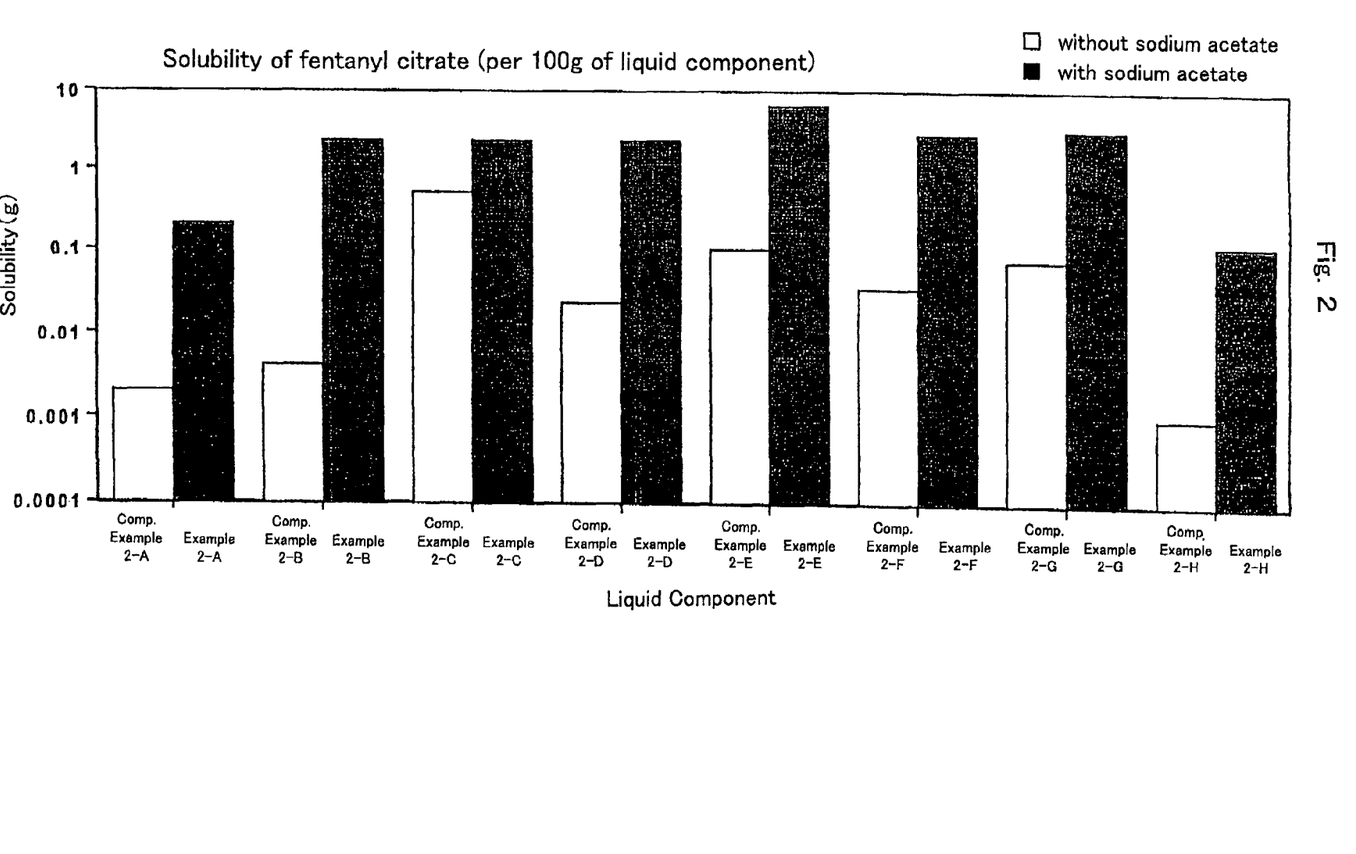
FIG. 2 shows solubility of fentanyl citrate as a basic drug salt in various liquid components. In the figure, open bar graphs indicate without addition of organic acids and closed bar graphs indicate with addition of organic acid salt of the present invention.

Liquid components, liquid paraffin (example 2-A), isopropylmyristate (example 2-B), crotamiton (example 2-C), triacetin (example 2-D), oleic acid (example 2-E), oleyl alcohol (example 2-F), triethyl citrate (example 2-G) and silicone oil (example 2-H), respectively, 10 g, sodium acetate 0.1 g and excess amount of fentanyl citrate were mixed well in the mortar for 30 minutes. Subsequently, the mixture was transferred into vials and stirred at room temperature for 12 hours. The mixture was filtered using the filter and concentration of fentanyl citrate in the filtrate was measured. Results are shown in FIG. 2.

Comparative Example 2

Liquid components, liquid paraffin (comparative example 2-A), isopropylmyristate (comparative example 2-B), crotamiton (comparative example 2-C), triacetin (comparative example 2-D), oleic acid (comparative example 2-E), oleyl alcohol (comparative example 2-F), triethyl citrate (comparative example 2-G) and silicone oil (comparative example 2-H), respectively, 10 g, and excess amount of fentanyl citrate were mixed well in the mortar for 30 minutes. Subsequently, the mixture was transferred into vials and stirred at room temperature for 12 hours. The mixture was filtered using the filter and concentration of fentanyl citrate in the filtrate was measured. Results are shown in FIG. 2.

Example 3

Figure 3:
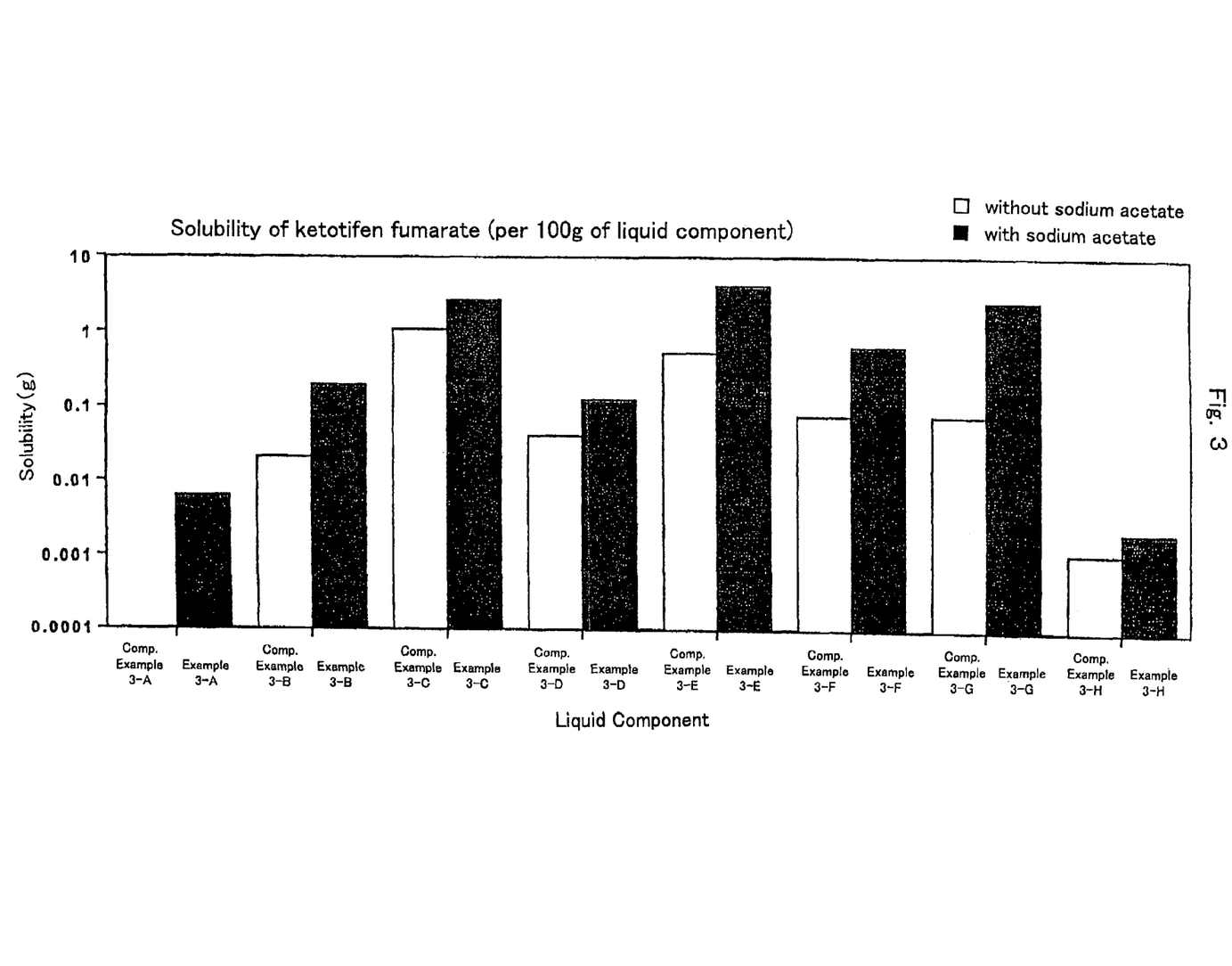
FIG. 3 shows solubility of ketotifen fumarate as a basic drug salt in various liquid components. In the figure, open bar graphs indicate without addition of organic acids and closed bar graphs indicate with addition of organic acid salt of the present invention.

Liquid components, liquid paraffin (example 3-A), isopropylmyristate (example 3-B), crotamiton (example 3-C), triacetin (example 3-D), oleic acid (example 3-E), oleyl alcohol (example 3-F), triethyl citrate (example 3-G) and silicone oil (example 3-H), respectively, 10 g, sodium acetate 0.1 g and excess amount of ketotifen fumarate were mixed well in the mortar for 30 minutes. Subsequently, the mixture was transferred into vials and stirred at room temperature for 12 hours. The mixture was filtered using the filter and concentration of ketotifen fumarate in the filtrate was measured. Results are shown in FIG. 3.

Comparative Example 3

Liquid components, liquid paraffin (comparative example 3-A), isopropylmyristate (comparative example 3-B), crotamiton (comparative example 3-C), triacetin (comparative example 3-D), oleic acid (comparative example 3-E), oleyl alcohol (comparative example 3-F), triethyl citrate (comparative example 3-G) and silicone oil (comparative example 3-H), respectively, 10 g, and excess amount of ketotifen fumarate were mixed well in the mortar for 30 minutes. Subsequently, the mixture was transferred into vials and stirred at room temperature for 12 hours. The mixture was filtered using the filter and concentration of ketotifen fumarate in the filtrate was measured. Results are shown in FIG. 3.

Example 4

Figure 4:
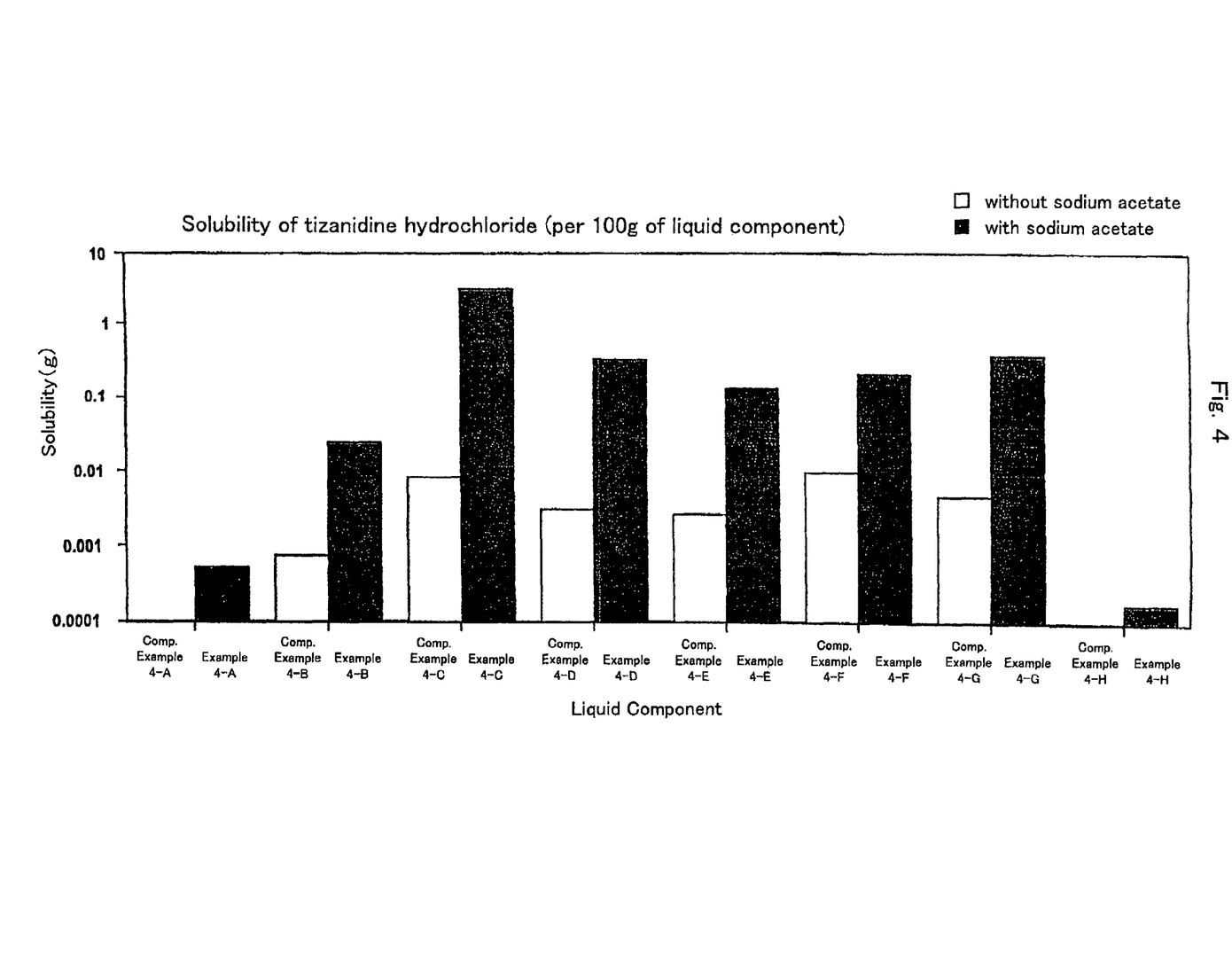
FIG. 4 shows solubility of tizanidine hydrochloride as a basic drug salt in various liquid components. In the figure, open bar graphs indicate without addition of organic acids and closed bar graphs indicate with addition of organic acid salt of the present invention.

Liquid components, liquid paraffin (example 4-A), isopropylmyristate (example 4-B), crotamiton (example 4-C), triacetin (example 4-D), oleic acid (example 4-E), oleyl alcohol (example 4-F), triethyl citrate (example 4-G) and silicone oil (example 4-H), respectively, 10 g, sodium acetate 0.1 g and excess amount of tizanidine hydrochloride were mixed well in the mortar for 30 minutes. Subsequently, the mixture was transferred into vials and stirred at room temperature for 12 hours. The mixture was filtered using the filter and concentration of tizanidine hydrochloride in the filtrate was measured. Results are shown in FIG. 4.

Comparative Example 4

Liquid components, liquid paraffin (comparative example 4-A), isopropylmyristate (comparative example 4-B), crotamiton (comparative example 4-C), triacetin (comparative example 4-D), oleic acid (comparative example 4-E), oleyl alcohol (comparative example 4-F), triethyl citrate (comparative example 4-G) and silicone oil (comparative example 4-H), respectively, 10 g, and excess amount of tizanidine hydrochloride were mixed well in the mortar for 30 minutes. Subsequently, the mixture was transferred into vials and stirred at room temperature for 12 hours. The mixture was filtered using the filter and concentration of tizanidine hydrochloride in the filtrate was measured. Results are shown in FIG. 4.

Example 5

Figure 5:
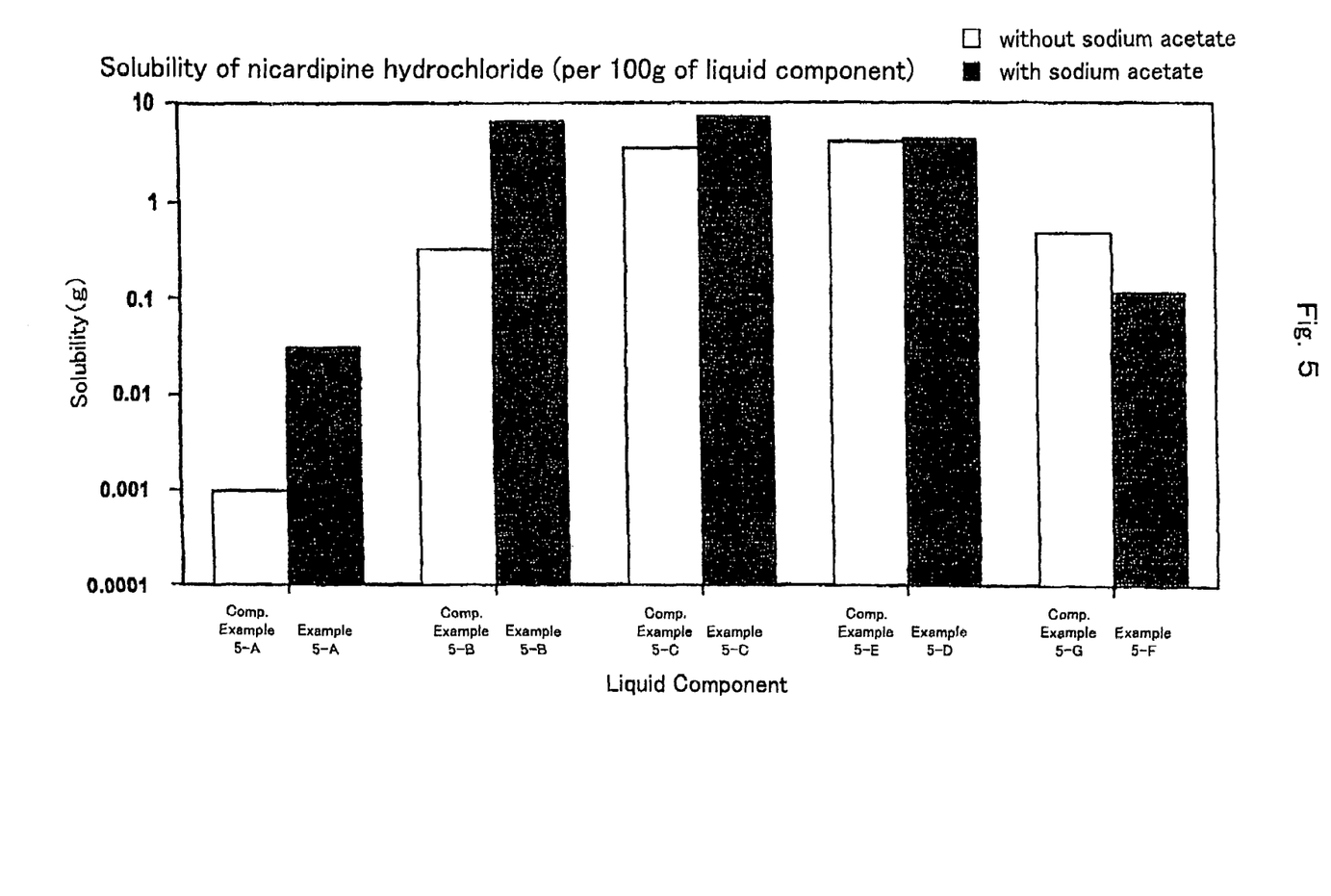
FIG. 5 shows solubility of nicardipine hydrochloride as a basic drug salt in various liquid components. In the figure, open bar graphs indicate without addition of organic acids and closed bar graphs indicate with addition of organic acid salt of the present invention. Proviso that a liquid component having solubility parameter above 13 $(cal/cm^3)^{1/2}$ is illustrated in the comparative example (comparative example 5-D or 5-F).

Liquid components, liquid paraffin (example 5-A), pirotiodecane (example 5-B) and propylene glycol (example 5-C), respectively, 10 g, sodium acetate 0.1 g and excess amount of nicardipine hydrochloride were mixed well in the mortar for 30 minutes. Subsequently, the mixture was transferred into vials and stirred at room temperature for 12 hours. The mixture was filtered using the filter and concentration of nicardipine hydrochloride in the filtrate was measured. Results are shown in FIG. 5.

Comparative Example 5

Liquid components, liquid paraffin (comparative example 5-A), pirotiodecane (comparative example 5-B), propylene glycol (comparative example 5-C), ethylene glycol (comparative example 5-E) and water (comparative example 5-G), respectively, 10 g, and excess amount of nicardipine hydrochloride were mixed well in the mortar for 30 minutes. Ethylene glycol having the solubility parameter of above 13 $(cal/cm^3)^{1/2}$ ($\delta$=14.5) (comparative example 5-D) and water ($\delta$=23.4) (comparative example 5-F), respectively, 10 g, sodium acetate 0.1 g and excess amount of nicardipine hydrochloride were mixed well in the mortar for 30 minutes. Subsequently, these mixtures were transferred into vials and stirred at room temperature for 12 hours. The mixtures were filtered using the filter and concentration of nicardipine hydrochloride in the filtrate was measured. Results are shown in FIG. 5.

As apparent from the results in FIG. 1-FIG. 4, solubility of the salt of basic drugs to the liquid component was increased by adding the organic acid salt of the present invention.

Further, as apparent from the result in FIG. 5, increased solubility of the salt of basic drugs to the liquid component by adding organic acid salt of the present invention was observed in the liquid component having the solubility parameter ranging from 7 to 13 $(cal/cm^3)^{1/2}$, and no effect was observed in the liquid component having the solubility parameter above 13 $(cal/cm^3)^{1/2}$.

Hairless Mouse Skin Permeability Test

Figure 6:
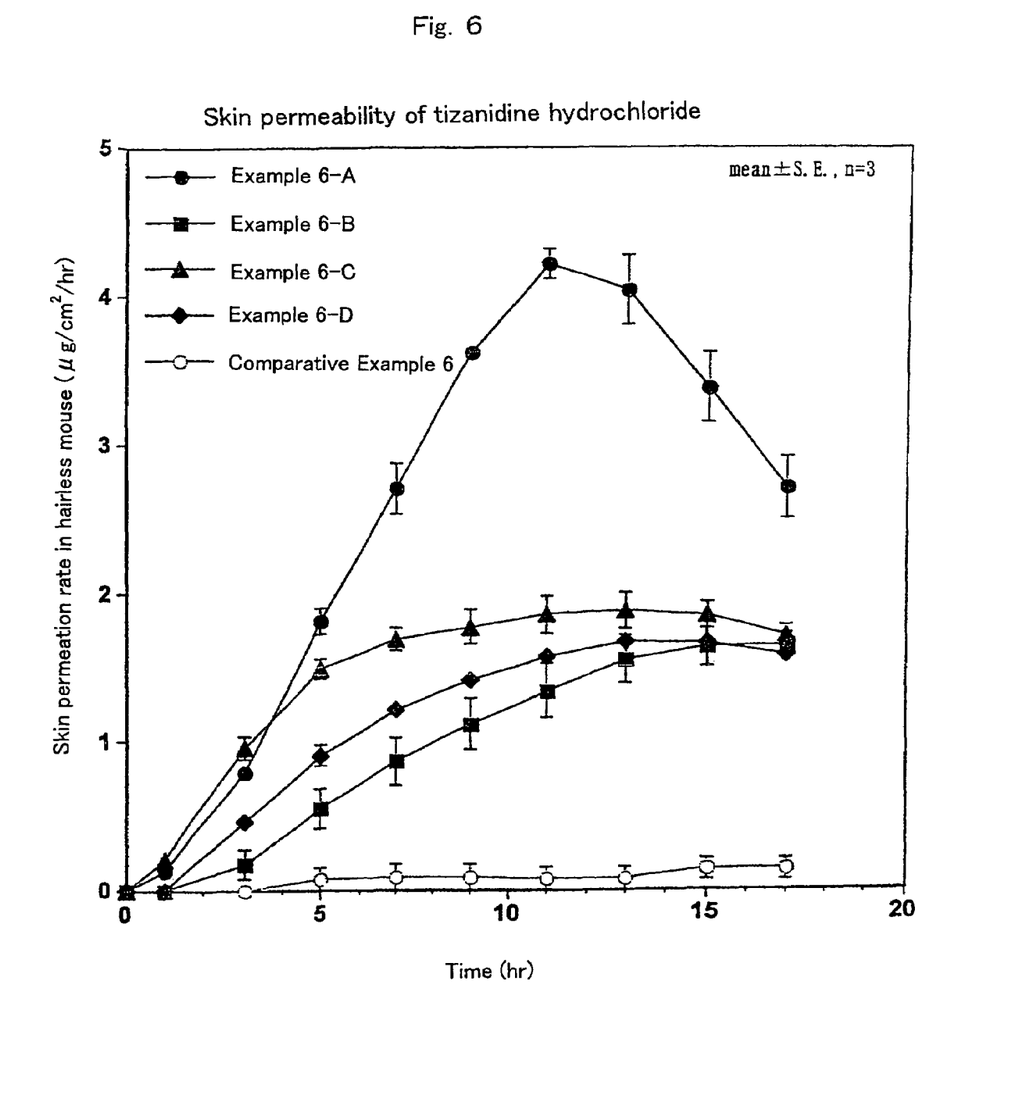
FIG. 6 shows skin permeability of patches of tizanidine hydrochloride as a basic drug salt using various organic salts. In the figure, close circles are a case using sodium acetate as an organic acid salt (example 6-A); close squares are a case using sodium propionate as an organic acid salt (example 6-B); close triangles are a case using sodium caprylate as an organic acid salt (example 6-C); and close rhombi are a case using sodium benzoate as an organic acid salt (example 6-D). Open circles shows a comparative example (comparative example 6) without using organic acid salt.
Figure 7:
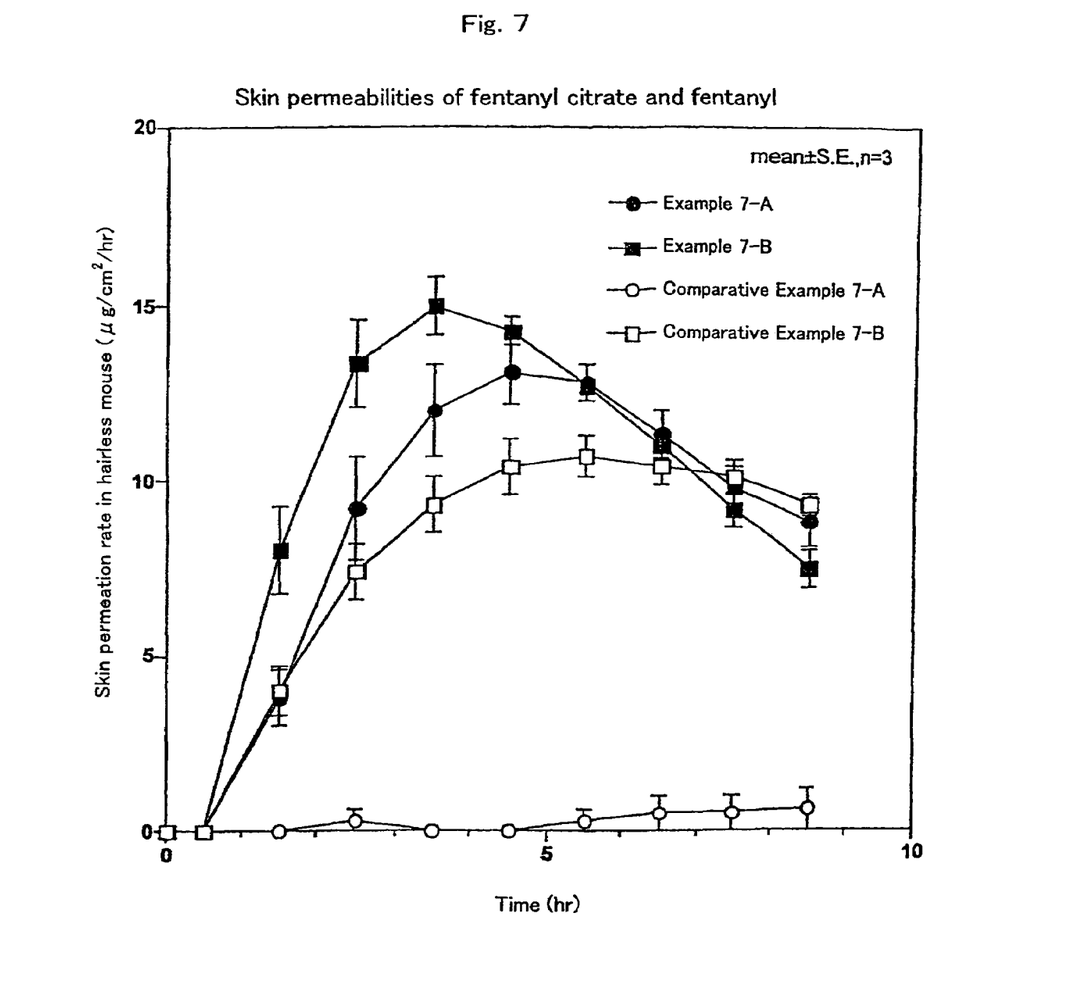
FIG. 7 is a graph showing the skin permeability of a patch using fentanyl citrate as a basic drug salt with sodium acetate and that of a patch using fentanyl as a basic drug (free) with acetic acid. In the figure, closed circles show a case using fentanyl citrate with sodium acetate (example 7-A) and open circles show a comparative example without sodium acetate (comparative example 7-A). Further, in the figure, closed squares show a case using fentanyl with acetic acid (example 7-B) and open squares show a comparative example without acetic acid (comparative example 7-B).
Figure 8:
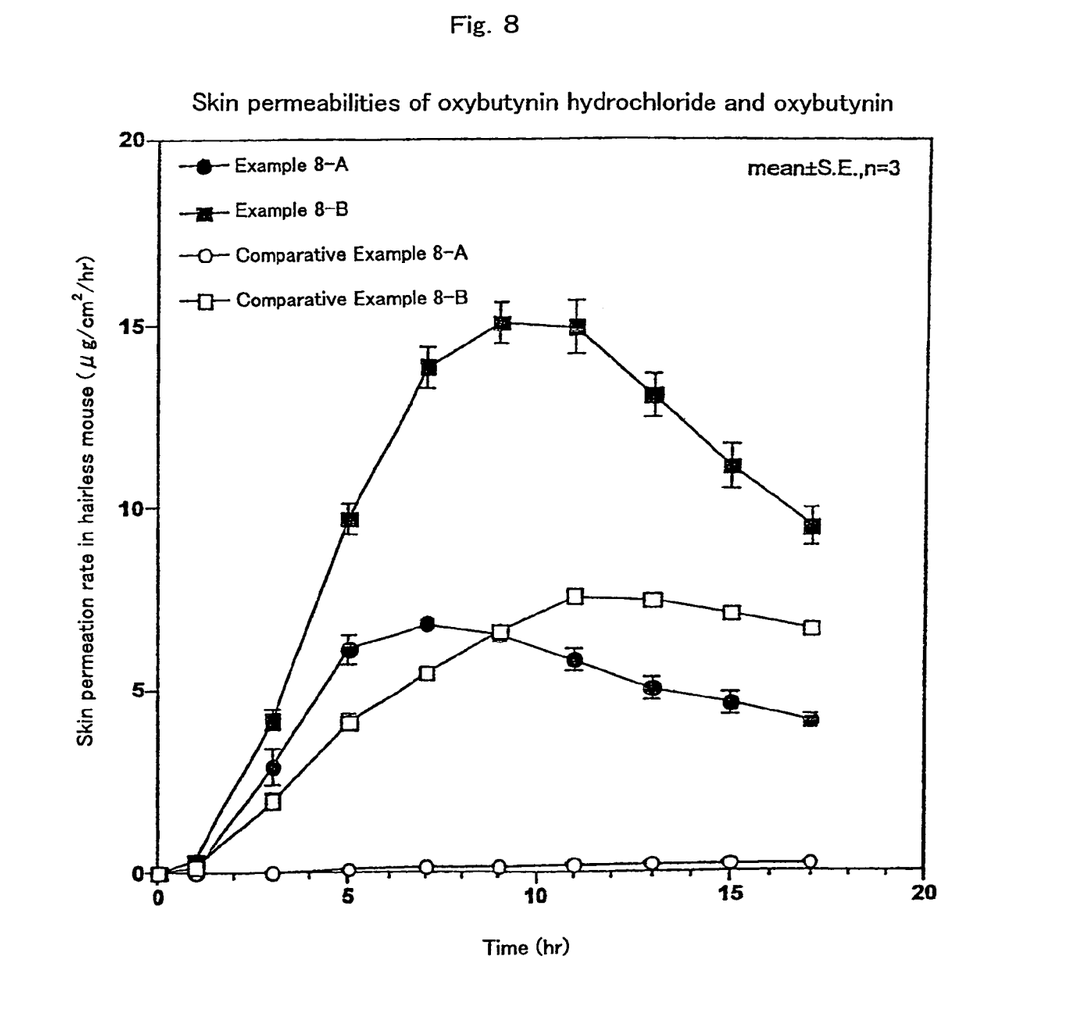
FIG. 8 is a graph showing the skin permeability of a patch using oxybutynin hydrochloride as a basic drug salt with sodium acetate and that of a patch using oxybutynin as a basic drug (free) with acetic acid. In the figure, closed circles show a case using oxybutynin hydrochloride with sodium acetate (example 8-A) and open circles show a comparative example without sodium acetate (comparative example 8-A). Further, in the figure, closed squares show a case using oxybutynin with acetic acid (example 8-B) and absorption comprising a combination of the basic drug salt, the organic acid salt and the liquid component having the solubility parameter ranging from 7 to 13 $(cal/cm^3)^{1/2}$, or the basic drug (free form), the organic acid (free form) and the liquid component having the solubility parameter ranging from 7 to 13 $(cal/cm^3)^{1/2}$.

Dorsal skin of hairless mouse was peeled off. Dermal side was prepared for the side of receptor phase and set in the flow-through cells (5 cm$^2$) in which warm water at 37° was circulated through the outer circumference. The preparation obtained in examples 6-A-6-D and comparative example 6; examples 7-A and 7-B and comparative examples 7-A and 7-B; and examples 8-A and 8-B and comparative examples 8-A and 8-B were strapped to the stratum corneum side. The physiological saline was used in the receptor phase and samples were collected at a rate of 5 ml/hour by sampling every 2 hours for 18 hours or every 1 hour for 9 hours. Flow rate of the receiver solution obtained at each time was exactly measured by high performance liquid chromatography, and flux permeation rate per hour was calculated, subsequently the skin flux permeation rate was determined by the following equation. Results are shown in FIG. 6-FIG. 8.

Skin flux permeation rate (μg/cm²/hr)=[sample concentration (μg/ml)×flow rate (ml)]/application area (cm²) of preparation

Example 6-A

| | |
|---|---|
| SIS | 26.0% |
| Hydrogenated rosin ester | 35.0% |
| Liquid paraffin | 31.6% |
| Crotamiton | 5.0% |
| Sodium acetate | 0.4% |
| Tizanidine hydrochloride | 1.5% |
| BHT | 0.5% |
| Total | 100.0% |

Tizanidine hydrochloride, sodium acetate, crotamiton and liquid paraffin were previously well mixed in the mortar, and mixed with polymer component dissolved in toluene. After spreading on the release paper, solvent was removed by drying, and laminated with the supporting material to prepare matrix patch of the present invention.

Example 6-B

The manner of Example 6-A was repeated except that sodium propionate was used as an organic acid, and other components and procedures were performed as same as in Example 6-A.

Example 6-C

The manner of Example 6-A was repeated except that sodium caprylate was used as an organic acid, and other components and procedures were performed as same as in Example 6-A.

Example 6-D

The manner of Example 6-A was repeated except that sodium benzoate was used as an organic acid, and other components and procedures were performed as same as in Example 6-A.

Comparative Example 6

The manner of Example 6-A was repeated except that no organic acid salt was used and amount of liquid paraffin was set as 32.0%, and other components and procedures were performed as same as in Example 6-A.

Example 7-A

| | |
|---|---|
| SIS | 26.0% |
| Hydrogenated rosin ester | 35.0% |
| Liquid paraffin | 29.5% |
| pirotiodecane | 3.0% |
| Sodium acetate | 2.0% |
| Fentanyl citrate | 4.0% |
| BHT | 0.5% |
| Total | 100.0% |

Fentanyl citrate, sodium acetate, pirotiodecane and liquid paraffin were previously well mixed in the mortar, and mixed with polymer component dissolved in toluene. After spreading on the release paper, solvent was removed by drying, and laminated with the supporting material to prepare matrix patch of the present invention.

Comparative Example 7-A

The manner of Example 7-A was repeated except that no organic acid salt was used and amount of liquid paraffin was set as 31.5%, and other components and procedures were performed as same as in Example 7-A.

Example 7-B

| | |
|---|---|
| SIS | 26.0% |
| Hydrogenated rosin ester | 35.0% |
| Liquid paraffin | 31.5% |
| Pirotiodecane | 3.0% |
| Acetic acid | 1.4% |
| Fentanyl | 2.6% |
| BHT | 0.5% |
| Total | 100.0% |

Fentanyl, acetic acid, pirotiodecane and liquid paraffin were previously well mixed in the mortar, and mixed with polymer component dissolved in toluene. After spreading on the release paper, solvent was removed by drying, and laminated with the supporting material to prepare matrix patch of the present invention.

Comparative Example 7-B

The manner of Example 7-B was repeated except that no organic acid was used and amount of liquid paraffin was set as 32.9%, and other components and procedures were performed as same as in Example 7-B.

Example 8-A

| | |
|---|---|
| SIS | 26.0% |
| Hydrogenated rosin ester | 35.0% |
| Liquid paraffin | 25.0% |
| Crotamiton | 5.0% |
| Sodium acetate | 3.0% |
| Oxybutynin hydrochloride | 5.5% |
| BHT | 0.5% |
| Total | 100.0% |

Oxybutynin hydrochloride, sodium acetate, crotamiton and liquid paraffin were previously well mixed in the mortar, and mixed with polymer component dissolved in toluene. After spreading on the release paper, solvent was removed by drying, and laminated with the supporting material to prepare matrix patch of the present invention.

Comparative Example 8-A

The manner of Example 8-A was repeated except that no organic acid salt was used and amount of liquid paraffin was set as 28.0%, and other components and procedures were performed as same as in Example 8-A.

Example 8-B

| SIS | 26.0% |
| Hydrogenated rosin ester | 38.0% |
| Liquid paraffin | 23.0% |
| Propylene glycol | 3.0% |
| pirotiodecane | 3.0% |
| Acetic acid | 2.0% |
| Oxybutynin hydrochloride | 5.0% |
| Total | 100.0% |

Oxybutynin hydrochloride, acetic acid, propylene glycol, pirotiodecane and liquid paraffin were previously well mixed in the mortar, and mixed with polymer component dissolved in toluene. After spreading on the release paper, solvent was removed by drying, and laminated with the supporting material to prepare matrix patch of the present invention.

Comparative Example 8-B

The manner of Example 8-B was repeated except that no organic acid was used and amount of liquid paraffin was set as 25.0%, and other components and procedures were performed as same as in Example 8-B.

As apparent from the results in FIG. 6-FIG. 8, skin permeability of the basic drug or its salt was increased by adding the organic acid or its salt of the present invention.

INDUSTRIAL APPLICABILITY

According to application of the preparations for percutaneous absorption of the present invention, drugs can be effectively absorbed into the circulating blood flow through the skin. In addition, side effects in the digestive system and adverse effects in the central nervous system occurred by rapid increase of blood concentration observed in the oral administration can be avoided. Further, the preparation is extremely low irritability to the skin and is especially useful as external preparations for percutaneous application.

The invention claimed is:

1. A percutaneous absorption preparation which is substantially free of water comprising a free base drug, an acetic acid and a nonaqueous liquid component having a solubility parameter ranging from 7 to 13 $(cal/cm^3)^{1/2}$ wherein the free base drug is one selected from the group consisting of oxybutynin and fentanyl.

2. The percutaneous absorption preparation which is substantially free of water according to claim 1 wherein the nonaqueous liquid component is one or more compounds selected from the group consisting of liquid paraffin, isopropyl myristate, crotamiton, triacetin, oleic acid, oleyl alcohol, triethyl citrate, silicone oil, propylene glycol, pirotiodecane or diethyl sebacate.

3. The percutaneous absorption preparation which is substantially free of water according to claim 1 or 2 wherein the percutaneous absorption preparation is a patch.

* * * * *